(12) United States Patent
Nishikawa

(10) Patent No.: US 8,090,182 B2
(45) Date of Patent: Jan. 3, 2012

(54) IMAGE RECONSTRUCTION DEVICE, IMAGE RECONSTRUCTION METHOD, IMAGE RECONSTRUCTION PROGRAM, AND CT APPARATUS

(75) Inventor: Yukihiro Nishikawa, Kyoto (JP)

(73) Assignee: National University Corporation Kyoto Institute of Technology, Kyoto-shi, Kyoto (JP)

( * ) Notice: Subject to any disclaimer, the term of this patent is extended or adjusted under 35 U.S.C. 154(b) by 363 days.

(21) Appl. No.: 12/514,579

(22) PCT Filed: Nov. 13, 2007

(86) PCT No.: PCT/JP2007/072339
§ 371 (c)(1),
(2), (4) Date: May 12, 2009

(87) PCT Pub. No.: WO2008/059982
PCT Pub. Date: May 22, 2008

(65) Prior Publication Data
US 2009/0279768 A1    Nov. 12, 2009

(30) Foreign Application Priority Data
Nov. 13, 2006    (JP) .................................. 2006-307058

(51) Int. Cl.
*G06K 9/00* (2006.01)
*G01N 23/00* (2006.01)
(52) U.S. Cl. ................................ 382/132; 378/8; 378/21
(58) Field of Classification Search .......... 382/128–133, 382/154, 266; 378/8, 4, 95, 21; 600/413, 600/425, 428
See application file for complete search history.

(56) References Cited

U.S. PATENT DOCUMENTS

| 4,641,328 | A   | * | 2/1987  | Fujise        | 378/8   |
|-----------|-----|---|---------|---------------|---------|
| 4,969,110 | A   | * | 11/1990 | Little et al. | 382/131 |
| 5,802,133 | A   | * | 9/1998  | Kawai et al.  | 378/4   |
| 6,470,066 | B2  | * | 10/2002 | Takagi et al. | 378/8   |
| 6,639,965 | B1  | * | 10/2003 | Hsieh et al.  | 378/8   |

(Continued)

FOREIGN PATENT DOCUMENTS

JP    60-17568 A    1/1985
WO    99/01065 A1    1/1999

OTHER PUBLICATIONS

Mehran Yazdia, Luc Gingras and Luc Beaulieu, "An Adaptive Approach to Metal Artifact Reduction in Helical Computed Tomography for Radiation Therapy Treatment Planning: Experimental and Clinical Studies", Int. J. Radiation Oncology Biol. Phys., 2005, vol. 62, No. 4, pp. 1224-1231.

(Continued)

*Primary Examiner* — Hoa Pham
(74) *Attorney, Agent, or Firm* — Roberts Mlotkowski Safran & Cole P.C.

(57) ABSTRACT

A computerized tomography apparatus and program for obtaining a cross-sectional image corresponding to projections are provided in which, for a temporary cross-sectional image f(x, y) obtained in some manner, an evaluation function E is defined which includes differences between projections calculated from f(x, y) and measured projections, and f(x, y) is changed in a manner which substantially decreases E. The computerized tomography apparatus and program are characterized in which a back projection operation, which is required by conventional computerized tomography, is not essentially required. The computerized tomography apparatus and program are particularly effective in removal or reduction of metal artifacts, aliasing artifacts and the like.

16 Claims, 9 Drawing Sheets

U.S. PATENT DOCUMENTS

| | | | |
|---|---|---|---|
| 6,873,678 B2 * | 3/2005 | Hoffman | 378/19 |
| 7,477,928 B2 * | 1/2009 | Acharya et al. | 600/428 |
| 2001/0028696 A1 | 10/2001 | Yamada et al. | |
| 2011/0142316 A1 * | 6/2011 | Wang et al. | 382/131 |

OTHER PUBLICATIONS

International Search Report for PCT/JP2007/072339 mailed Feb. 26, 2008.

Loose et al., On few-view tomographic reconstruction with megavoltage photon beams; Am. Assoc. Phys. Med. 28 (8), Aug. 2001; 1679-1688.

Haneishi et al., Analysis of the cost function used in simulated annealing for CT image reconstruction; Applied Optics, Jan. 10, 1990; vol. 29, No. 2; pp. 259-265.

* cited by examiner

FIG.5
(a)
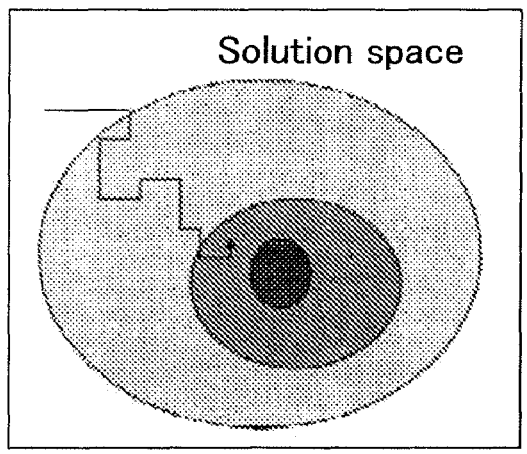
(b)
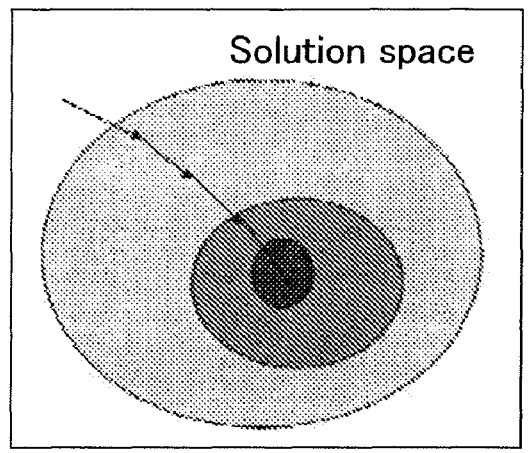

FIG.6

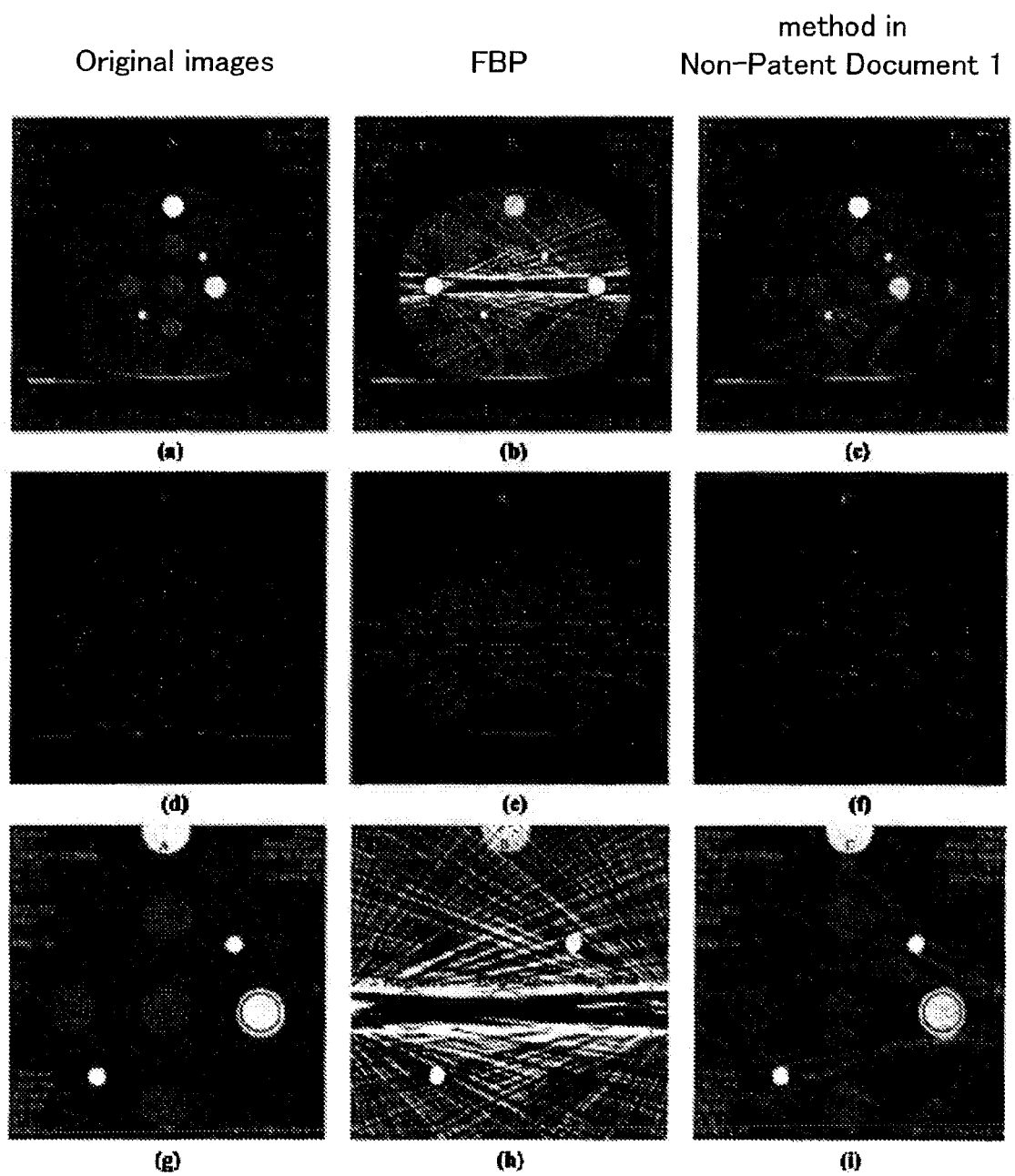

Fig. 5. Phantom test: (a) original phantom image without inserting metallic rods; (b) presence of artifacts because of metallic rods; (c) result of artifact reduction algorithm; (d) result of applying an automatic edge detection algorithm on original phantom image, (e) on phantom image with metallic rods, and (f) on artifact reduction image; (g) computing the mean and SD for three objects in the middle of the phantom in original phantom image, (h) in phantom image with metallic rods, and (i) in artifact reduction image.

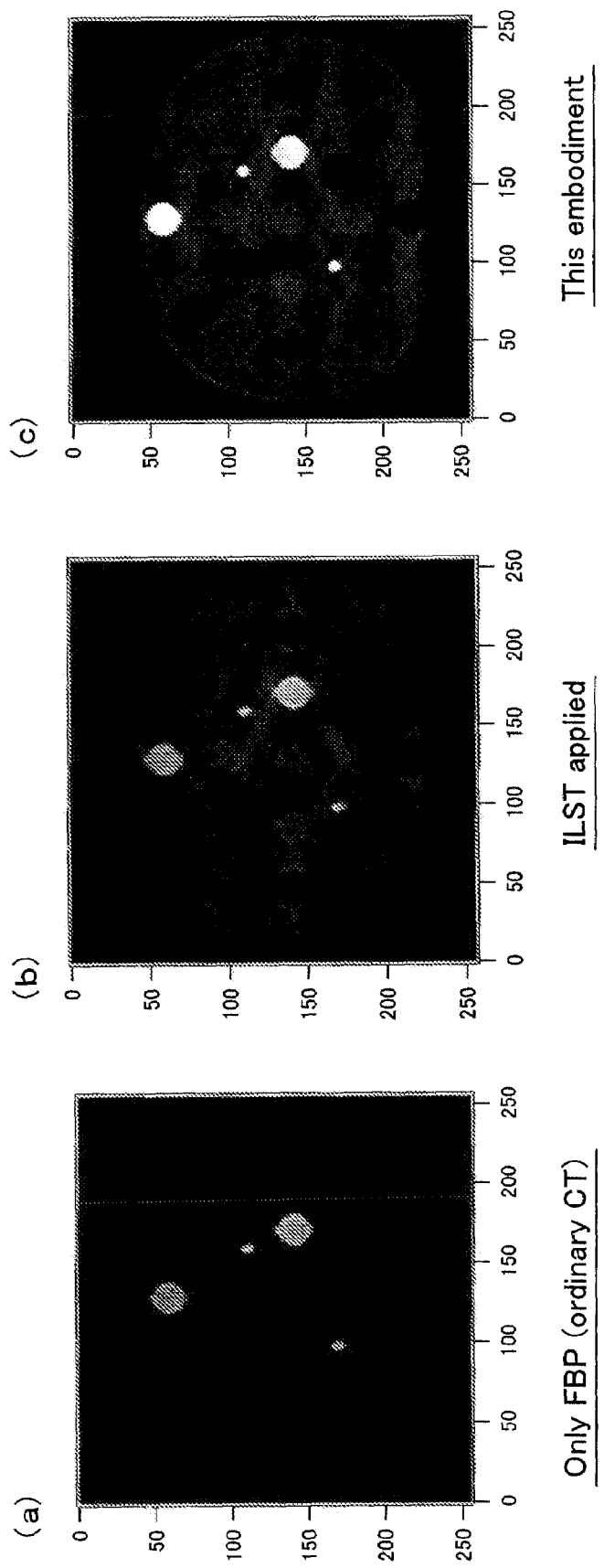

IMAGE RECONSTRUCTION DEVICE, IMAGE RECONSTRUCTION METHOD, IMAGE RECONSTRUCTION PROGRAM, AND CT APPARATUS

TECHNICAL FIELD

The present invention relates to a technique of reconstructing a cross-sectional image of an object from the radiographic projections of the object.

BACKGROUND ART

Computerized tomography (CT) is a technique of reconstructing a cross-sectional image of an object from the radiographic projections of the object. FIG. 1 is a diagram schematically showing a typical X-ray CT apparatus.

In the typical CT apparatus, an X-ray source is moved around a target object, and irradiates X-rays to obtain the projections of the target object in many different directions. A cross-sectional image is obtained by subjecting the projections thus obtained to a computational operation, so-called reconstruction. The Filtered Back-Projection method (FBP) is commonly used to reconstruct a cross-sectional image from the projections. FBP is a kind of a transformation operation. In FBP, the projections are subjected to a filtering essentially equivalent to the differential filtering, followed by "back projection," in which each projection is projected back along the original projection direction, thereby a cross-sectional image is obtained. In this case, the differential filtering usually amplifies noise or errors, which can be the source of artifacts (errors or false images which do not actually exist). Moreover, the back propagation operation spreads the artifacts thus created allover the cross-sectional image. Therefore, in CT, the artifacts often are not limited within a local portion around the source of the artifacts, and impairs the entire cross-sectional image, resulting in a fatal flaw.

Most artifacts are caused by the filtering operation and/or the back projection operation involved in FBP. Therefore, if FBP is not used, a cross-sectional image substantially can be free from most of artifacts. As a method of calculating a cross-sectional image other than FBP, the Algebraic Reconstruction Technique (ART) is historically important. ART was a major reconstruction method before FBP was proposed. In ART, the process of reconstruction is considered as a fitting problem where the cross-sectional image is a parameter and the projections are a target dataset to be fit. The cross-sectional image is iteratively modified so that projections (p) calculated from the cross-sectional image fit projections ($p_0$) experimentally obtained. A feature of ART is that a cross-sectional image is asymptotically modified so that $(p-p_0)$ becomes zero. ART usually requires a vast computation time in comparison to FBP. Therefore, ART is currently used only for particular applications (the analysis of seismic waves, etc.). Although ART does not produce as extreme artifacts as FBP does, FBP often provides a more natural cross-sectional image than ART does.

Besides the filtering operation and the back projection operation, artifacts may be caused by a lack or shortage of data in projections. It is known that a lack or shortage of data often results in a fatal artifact especially in FBP. Other reconstruction techniques based on fitting, such as ART, are expected to be more robust against a lack or shortage of data than FBP. However, a lack of data is known to make CT an extremely "ill-posed problem," under which it is essentially difficult to obtain reasonable solutions. One of the reasons why ART often fails in fitting is that ART uses $(p-p_0)$ for the target function of fitting. So it is quite natural to consider the use of the $(p-p_0)^2$ instead of $(p-p_0)$. In these cases, the least square method is one of the most popular way to minimize $(p-p_0)^2$. In the least square method, the inversion of a square matrix whose elements on one side is equal to the number of parameters is employed. Parameters in CT are values of pixels in the cross-sectional image, and therefore, the number of the parameters is huge, If a cross-sectional image has 1000× 1000 pixels, the number of the parameters becomes a million, and the number of elements in the matrix is as huge as a trillion. Therefore, if the ordinary least square method is used, the matrix is too huge to calculate. Instead of the ordinary least square method, the Simultaneous Iterative Reconstruction Technique (SIRT) and the Iterative Least Square Technique (ILST) have been proposed. In these techniques, the calculation of a cross-sectional image is considered as a fitting problem as in ART. FBP is utilized as an inverse operation to calculate the cross-sectional image from projections partway through the calculation in both SIRT and WLST so as to circumvent the use of the ordinary least square method as described above. Therefore, none of SIRT and ILST does not substantially solve the problems involved with the filtering operation and the back projection operation as in FBP. This is probably why there have been reports that SIRT and ILST just "reduce" artifacts.

Non-Patent Document 1: Yazdi M., Gingras L., Beaulieu L., An adaptive approach to metal artifact reduction in helical computed tomography for radiation therapy treatment planning: experimental and clinical studies, Int J Radiat Oncol Biol Phys, 62: 1224-1231, 2005.

DISCLOSURE OF THE INVENTION

Problems to be Solved by the Invention

As can be seen from the discussion above, no use of FBP and robustness against a lack of data are important so as to obtain a cross-sectional image free of artifacts. To achieve this, it is easily contemplated that a square error may be used as an evaluation function for fitting without using FBP as in ART. Nevertheless, the artifact problem of CT has not been substantially solved, since this simple idea cannot be straightforwardly realized. Firstly, the amount of calculation of a cross-sectional image by fitting is too huge to calculate quickly. It is essentially required to appropriately speed up the calculation. Secondly, the least square method, as a fitting algorithm, is weak (not effective) against "ill-posed" problems. Therefore, any extension of the existing algorithms (ILST, etc.) based on the least square method would not be able to solve the artifact problem. Thirdly, other existing algorithms as well as SIRT and ILST cannot completely eliminate the necessity of FBP.

Solution to the Problems

A first novelty of the present invention is to employ Simulated Annealing (SA) as a fitting method. SA is a known technique, which requires a long time to perform fitting, and is inherently considered not to be not suitable for CT. Despite this, by the sue of SA in CT, a cross-sectional image can be calculated by minimizing square errors without using FBP. SA is also stable even when fitting is performed under ill-posed conditions, such as a lack of data or the like. Also in this regard, the present invention is advantageous in terms of a fundamental solution to artifacts. In view of the properties above, the present invention has an important novelty that a fundamental solution to artifacts is obtained by applying SA to CT. When SA is simply applied to CT, we need to iterate the calculation of projections from a cross-sectional image so many times. The amount of the calculation of projections from a cross-sectional image is substantially the same as that of FBP. When SA is applied to CT, it takes several million times as long a time as that of FBP. The calculation time can be of the order of "years" even if a state-of-the-art high-speed computer is used. In the present invention, this problem is solved by significantly reducing the amount of calculation by transformation of expressions. This solution is a technique required when SA is applied to CT, which is an important feature of the present invention.

A second novelty is the introduction of a smoothing term and an entropic term, which actively destroy artifacts, into an evaluation function for fitting in addition to square errors. In conventional CT, only a difference between p and $p_0$ or their square errors is employed. In this case, there is always a possibility that a more satisfactory result (small errors) of fitting can be achieved while artifacts are left. Actually, this is often the case. Specifically, it is commonly expected that artifacts would be canceled with other artifacts. That is one of the reasons for the difficulties to eliminate artifacts. Even in the present invention, if only square errors are included in an evaluation function, artifacts were not completely eliminated. This fact indicates that another term is desired in addition to square errors so as to obtain a cross-sectional image free of artifacts. In the present invention, an entropic term and a smoothing term are introduced on the basis of statistical mechanics. These terms mathematically represent a natural requirement that a cross-sectional image should be a "smooth" and "natural" gray image. The entropic term induces fitting so as to destroy artifacts and uniformize image quality of an entire cross-sectional image. The smoothing term suppresses the granular pattern of a cross-sectional image which is caused by the entropic term. By introducing the both terms, a natural cross-sectional image free of artifacts can be obtained. Although the entropic term and the smoothing term can each reduce artifacts singly, a combination thereof is found to be more effective.

Note that the term "beam of radiation" as used herein refers to electromagnetic waves, such as X-rays, visible light and radio waves, particle beams including electrons or charged particles, sound waves, which are vibration of a medium, and the like, in a broader sense than the general definition.

Effect of the Invention

A first effect of the present invention is to reduce artifacts which are caused by a lack of data. Examples of a problem caused by a lack of data includes a case where an object to be observed has an opaque portion, a case where there is a limit on a projection angle, a case where projection angular intervals are not uniform, a case where three-dimensional CT (cone beam CT, helical scan CT, etc.) is performed, and the like.

In particular, it has been demonstrated that metal artifacts which appear when an object to be observed has an opaque portion can be reduced. The term "metal artifact" means that when there is an opaque portion (in many cases, a metal portion) with respect to X-rays in an object to be observed, an entire cross-sectional image (not only the opaque portion) obtained by CT is destructively disturbed. Metal artifacts are caused by a discontinuous change in luminance of a projection at an opaque portion, and a lack of information at the opaque portion. When the differential filtering is applied to the opaque portion in course of FBP, a discontinuous change in luminance takes an extraordinary value. Then, the extraordinary value is radially extended to be a streak artifact via the back protection operation. Moreover, a lack of information causes an unexpected contrast at the portions which are not directly related to the opaque portion. Since the present invention does not use FBP and employ SA which is stable against the lack of information, it is easily understood that the present invention is effective in removal of metal artifacts.

The present invention may be particularly useful for cone beam or helical scan in terms of practical use. Both are called three-dimensional CT, and are currently rapidly becoming widespread. However, it is known that peculiar artifacts appear in three-dimensional CT. The causes of the artifacts have been identified, but have not been solved. In the case of cone beam, the cause of the artifacts is a lack of data. In the case of cone beam, conditions under which a complete cross-sectional image can be obtained cannot be satisfied, so that artifacts appear due to a lack of data. In the case of helical scan, the fundamental cause of artifacts is a back projection operation. The geometric anisotropy (helix) of the system of helical scan affects a filtering operation and a back projection operation, resulting in windmill artifacts. Since the present invention does not require a filtering operation or a back projection operation, and is robust against a lack of data, the present invention can solve the problems with three-dimensional CT.

Examples of a case where projection angles are not uniform include analysis of Earth's interior by CT using seismic waves, and analysis of an atmospheric state by CT using radio waves from an artificial satellite. These are known as typical cases where FBP cannot be utilized. It is expected that the present invention may be able to improve the accuracy of analysis.

A second effect of the present invention is to increase a rate at which projections are taken and decrease the dose of X-rays. Since SA is stable against a lack or shortage of data, the present invention also inherits this feature. In the case of CT, the case where the number of projection angles is small is one of the cases of a shortage of data. Thus, the utilization of the present invention can reduce the number of projection angles as compared to conventional CT. The number of projection angles corresponds to the number of projections in which the object is irradiated. So, the number of projections is proportional to the imaging time and the dose. Therefore, a reduction in the number of projections leads to a decrease in the imaging time and the dose.

There is also a shortage of data when the image quality of projections is poor (low S/N ratio), for example. It has been demonstrated that the present invention is relatively stable even in such a case. If a decrease in the image quality of projections can be tolerated, this also leads to a reduction in the imaging time and the dose. Also, the present invention would contribute to an improvement in image quality in SPECT and PET in which the S/N ratio is extremely low.

A third effect of the present invention is that a luminance value of a cross-sectional image can be determined with high accuracy. The present invention provides a cross-sectional image which substantially faithfully reproduces the measured projections. The accuracy of reproduction is higher by about two orders of magnitude than that of FBP. This is a benefit of the fitting algorithm which minimizes square errors. The higher accuracy of determination of a luminance value guarantees the quantitativeness of the cross-sectional image and allows a measurement of density using the luminance value. This feature can be used for an improvement in accuracy of measurement of bone density. Also, this would contribute to an improvement in accuracy of detection of a pathological change (an organ containing a tumor, etc.).

A fourth effect of the present invention is that a cross-sectional image obtained by the present invention has a higher contrast than that of FBP. As described in the third effect, the present invention has the high accuracy of determination of a luminance value. As its subsidiary effect, the contrast of a cross-sectional image becomes higher. A higher contrast tends to lead to a higher apparent spatial resolution. As a result, a cross-sectional image obtained by the present invention has higher image quality than that of the conventional art. Notably, this effect allows the present invention to be useful for not only CT under special conditions or for special applications, but also ordinary CT.

BRIEF DESCRIPTION OF THE DRAWINGS

FIG. 5(a) is a schematic diagram of a fitting process of steps (I) to (VI). FIG. 5(b) is a schematic diagram of a fitting process of steps (1) to (9).

FIG. 6 is the result of a technique described in Non-Patent Document 1.

FIG. 10 is a diagram showing artifacts and an artifact reducing effect of the present invention in the case with a limit on an angle.

BEST MODE FOR CARRYING OUT THE INVENTION

First Embodiment

Figure 1:
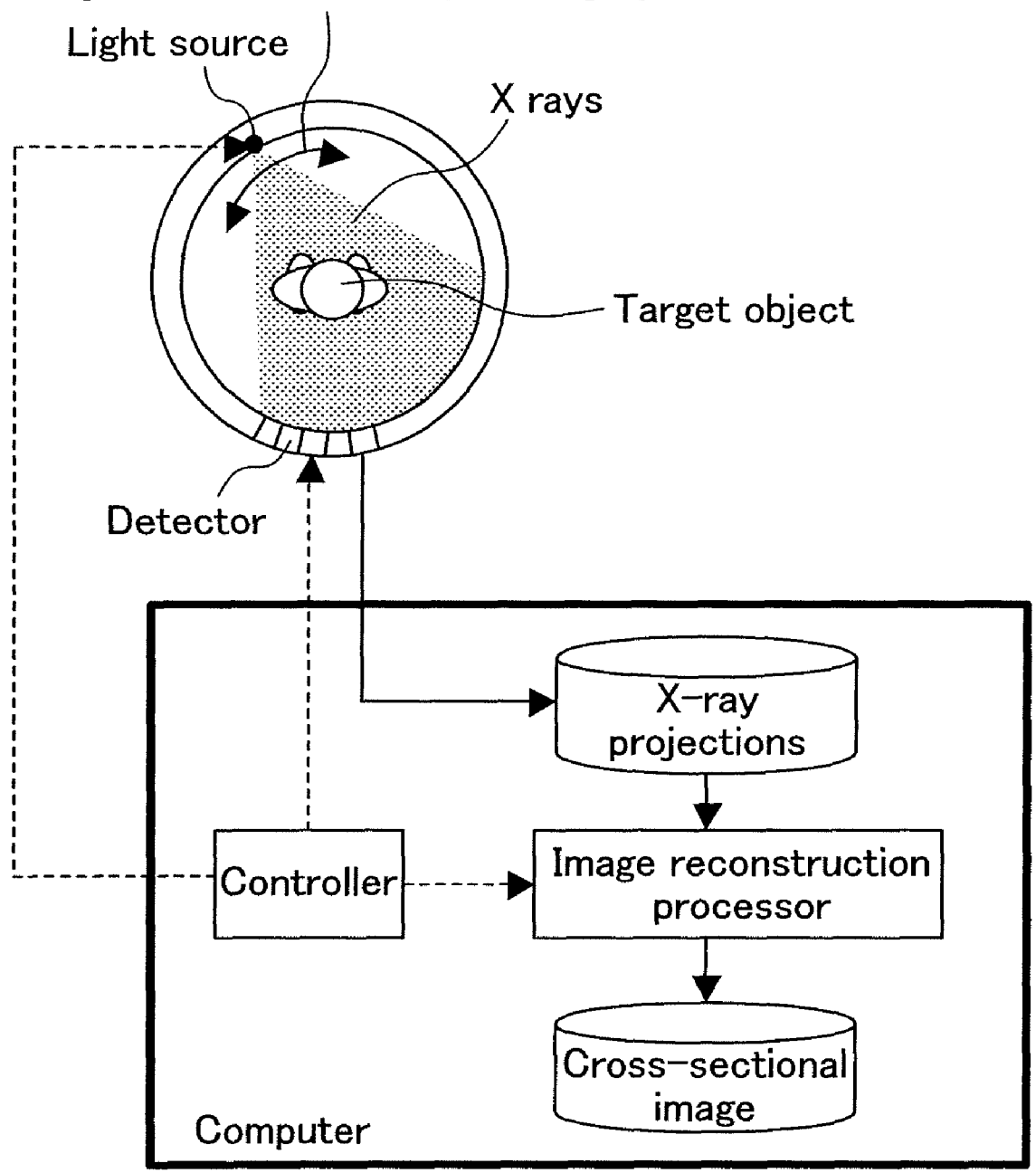
FIG. 1 is a schematic illustration of an X-ray CT apparatus.

FIG. 1 shows a schematic diagram of an X-ray CT apparatus according to an embodiment of the present invention. The X-ray CT apparatus includes an imaging unit and a computer. The imaging unit includes a light source for irradiating a target object (usually X-rays), and a detector for X-rays transmitted through the target object. The imaging unit obtains projections by emitting X-rays toward the target object in many different directions. The computer includes a controller for the entire X-ray CT apparatus, and an image reconstruction processor for generating a cross-sectional image of a region of interest of the target object based on X-ray projections obtained by the imaging unit. Note that the configuration of FIG. 1 is common to this and the following embodiments, but the image reconstruction processors of each embodiment performs different process.

The image reconstruction processor of this embodiment employs Simulated Annealing (SA) as a fitting method for obtaining a cross-sectional image from projections. Firstly, a framework of Simulated Annealing (SA) will be described. SA is a fitting algorithm derived from a Monte Carlo method, and is characterized in that the fitting is performed based on random numbers, and in that virtual energy and virtual temperature are handled in the analogy to thermodynamics. SA is a known technique, which is performed in steps (i) to (vi).

(i) A parameter is randomly chosen, and then, the parameter is changed based on a random number (random number).

(ii) Evaluation is performed after the changing. A virtual energy E is considered as an evaluation function. In typical SA methods, E is taken as the sum of square errors. The change in E between before and after the changing is represented by ΔE (evaluation).

(iii) If the result of evaluation is improved (ΔE<0), the changing is accepted (changing).

(iv) If the result of evaluation is worsened, the changing is accepted in a probability of exp(−ΔE/T).

(v) The temperature T is decreased by a small amount.

(vi) The procedure above is repeated from (i).

In SA, since the changing is accepted according to Boltzmann statistics as indicated in (iv) if the result of evaluation is worsened, the possibility of escaping from a local minimum of ΔE is secured. Therefore, the method can reach a global solution without trapping in a local minimum, and therefore, can stably function even under ill-posed conditions for fitting. Also, by gradually decreasing T, the method gradually approaches a global solution (soft landing). A set of (i) to (v) is referred to as a single Monte Carlo step. In SA, the Monte Carlo step is infinitely repeated, the fitting process progresses. A time required for the calculation is obtained by a time required for one Monte Carlo step × a required number of times of the Monte Carlo steps. The required number of times of the Monte Carlo steps is proportional to the number of parameters (or the degree of freedom).

Figure 3:
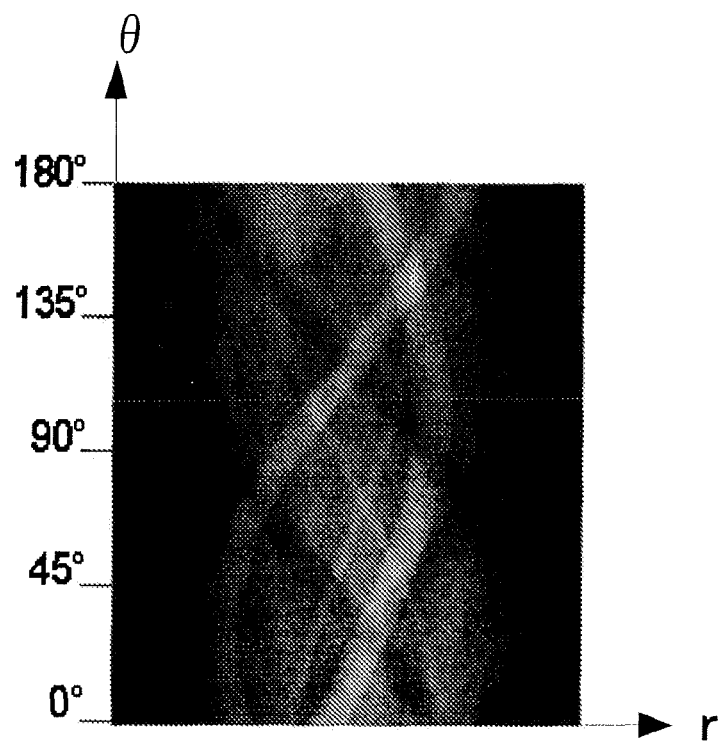
FIG. 3 shows a typical example of $p_0(r, \theta)$, where the abscissa and ordinate are respectively the projection angle and the channel portion of a detector.

Next, this embodiment will be described according to the claims. If CT is considered as a fitting problem, a fitting parameter is a cross-sectional image (f(x, y)). Data to be fit is projections ($p_0(r, \theta)$) where r indicates a channel position of a one-dimensional detector used in the imaging unit, and θ indicates a projection angle. A definition of coordinates is shown in FIG. 3. $p_0(r, \theta)$ is a set of data which is the measuring projections while changing the angle θ, and can represent a two-dimensional image if it is plotted in a graph where the horizontal axis represents r and the vertical axis represents θ. Such data is referred to as a sinogram. A typical sinogram is shown in FIG. 3.

Roughly speaking, CT is a technique of obtaining a cross-sectional image from a sinogram. In this embodiment, square errors between a temporary cross-sectional image f(x, y) and the measured projections $p_0(r, \theta)$ are used. In order to calculate the square errors, projections (p(r, θ)) are calculated from f(x, y) by:

$$p(r, \theta) = \sum_s f(r\cos\theta - s\sin\theta, r\sin\theta + s\cos\theta) \qquad \text{[Expression 101]}$$

Figure 2:
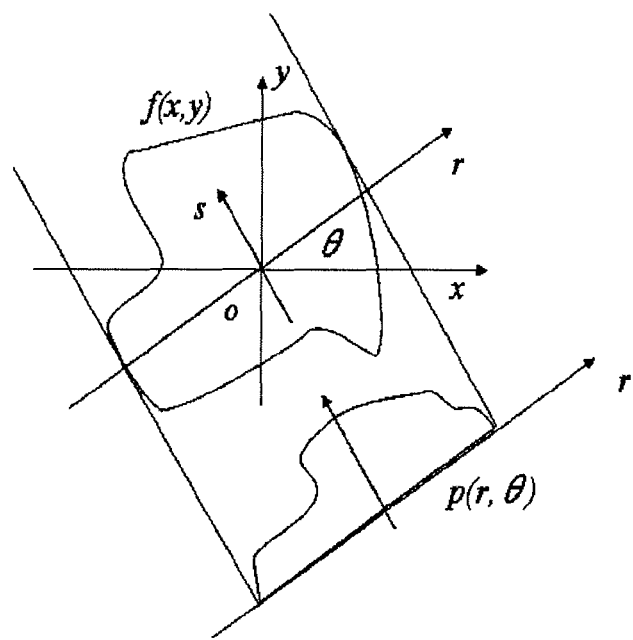
FIG. 2 is a schematic diagram showing a relationship between a cross-sectional image f(x, y) and a projection p(r, θ).

Expression 101 represents the calculation of a projection of f(x, y) along a direction s by summing on s in FIG. 2. By using p(r, θ) thus obtained, the sum of square errors H can be calculated as follows:

$$H = \sum_{r,\theta} \{p(r, \theta) - p_0(r, \theta)\}^2 \qquad \text{[Expression 102]}$$

Figure 4:
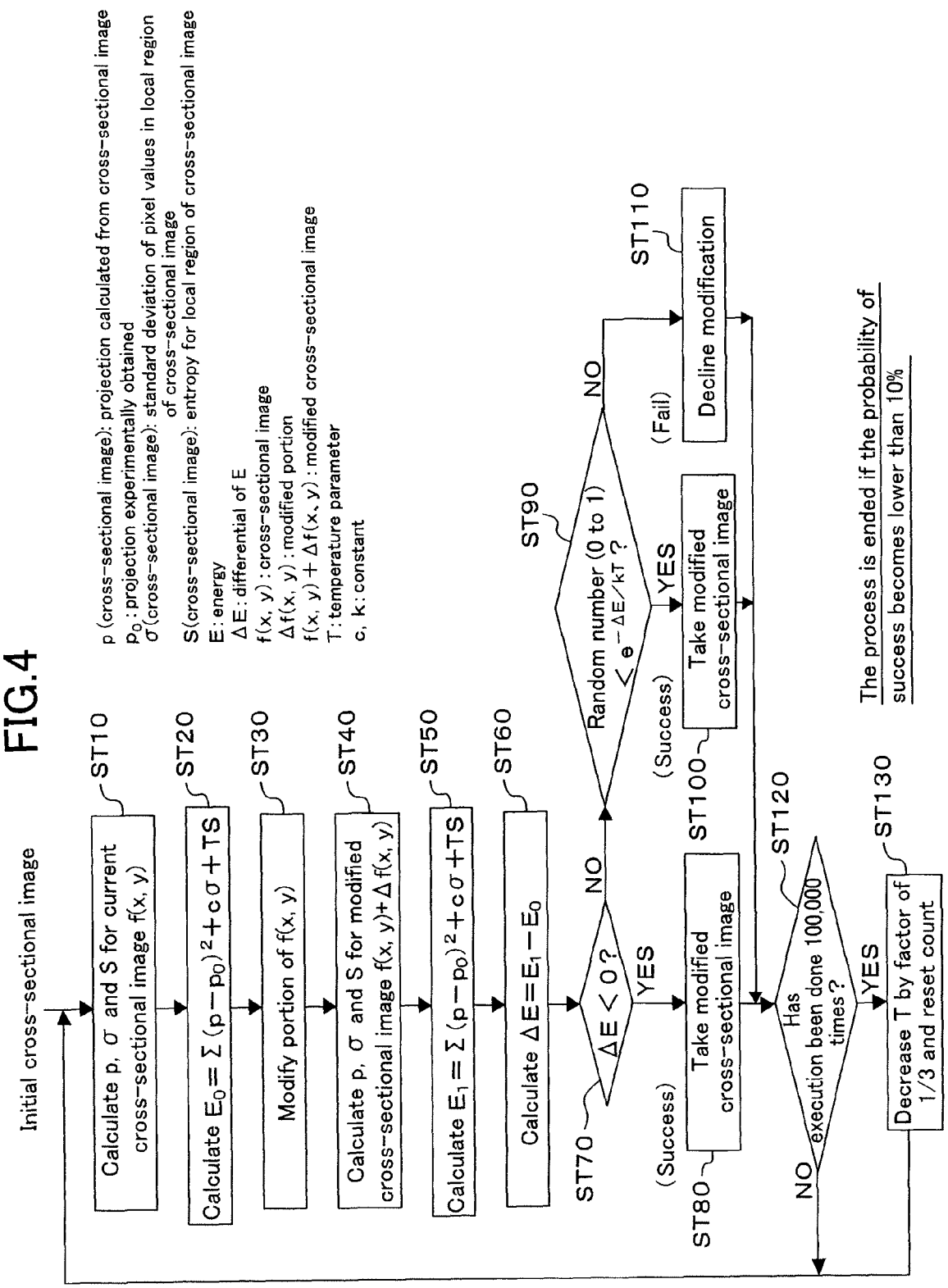
FIG. 4 is a flowchart showing a basic procedure of the present invention.

In typical fitting, Expression 102 is directly used as the virtual energy E. This embodiment is characterized in that a smoothing term and an entropic term are introduced in addition to H. The virtual energy E is defined as follows:

$$E = H - TS + c\sigma \quad \text{[Expression 103]}$$

where T represents a virtual temperature (temperature parameter), S represents an entropy, σ represents a standard deviation of pixel values, and c represents a coefficient which represents the strength of the smoothing term. In Expression 103, TS is an entropic term and cσ is a smoothing term. The definitions and calculation methods of S and C will be described below. In this embodiment, a cross-sectional image is calculated in accordance with a procedure as shown in FIG. 4 using these expressions.

Step (a): An evaluation function (hereinafter referred to as an "energy") ($E_0$) is obtained with respect to a temporary cross-sectional image f(x, y) which is prepared in some manner (ST10 and ST20).

Step (b): ($x_0$, $y_0$) and Δμ are selected using random numbers, and a portion of the cross-sectional image f(x, y) is modified (ST30).

Step (c): An evaluation function $E_1$ is obtained with respect to the modified cross-sectional image f(x, y) (ST40 and ST50).

Step (d): A differential (ΔE) between the energy ($E_0$) and the energy ($E_1$) is obtained (ST60).

Step (e): It is determined whether or not the modification is accepted, based on an acceptance function (typically Boltzmann statistics) using the differential (ΔE) and the temperature parameter (T) (ST70 to ST110).

Step (f): Control returns to step (a) (ST120).

Step (g): The value of the virtual temperature (T) is changed every time the number of iterations of steps (a) to (f) reaches a predetermined value (ST130).

Step (h): It is determined whether or not the result of determination in step (e) satisfies predetermined stop conditions. If the result of this determination is positive, the process is ended. Here, it is assumed that the change is a "success" if ST80 or ST100 is executed, and is a "failure" if ST110 is executed. If the probability of success becomes lower than 10% (this value is adjustable appropriately), the process is ended. An estimated cross-sectional image at the end of the process is considered as a cross-sectional image of the target object, which may be displayed on a display of the computer or may be recorded into a recording medium.

A series of operations from step (a) to step (h) corresponds to claim 12. In this embodiment, these operations are performed by the image reconstruction processor of FIG. 1.

These operations correspond to the basic steps (i) to (vi) of SA as follows: step (b) corresponds to (i); steps (a), (c) and (d) correspond to (ii); step (e) includes (iii) and (iv); step (g) corresponds to (v); and step (f) corresponds to (vi). Therefore, in this embodiment, SA is faithfully applied to CT.

Note that the determination of whether to end the process in step (h) may not be performed in the image reconstruction processor of FIG. 1. Estimated cross-sectional images may be successively displayed on a display of the computer, and a user who views the images may instruct the computer to end the process.

Second Embodiment

The virtual energy E indicated by Expression 103 is calculated by calculating the sum of a series with respect to s, r and θ via Expression 101 and Expression 102. A triple integral (the sum of a series) is calculated, which takes a considerably long time. In other words, it takes a long time to calculate one Monte Carlo step. In addition, CT has a huge number of parameters. As a result, a total calculation time required for execution of SA is of the order of years even if a state-of-the-art computer is used.

Therefore, in this embodiment, instead of calculating E, only ΔE, which is the difference when a change is made, is mainly calculated as follows:

$$\Delta E = \Delta H + c\Delta\sigma - T\Delta S \quad \text{[Expression 104]}$$

Now, a change in a temporary cross-sectional image f(x, y) is represented as Δf(x, y). The change Δf(x, y) is a cross-sectional image which has a value of Δμ only at a coordinate point ($x_0$, $y_0$) and zero elsewhere. A projection Δp(r, θ) of Δf(x, y) can be calculated by the same method as that of Expression 101. By using Δp(r, θ), ΔH can be calculated as follows:

$$\Delta H = \sum_{r,\theta} \{p(r,\theta) + \Delta p(r,\theta) - p_0(r,\theta)\}^2 - \quad \text{[Expression 105]}$$

$$\sum_{r,\theta} \{p(r,\theta) - p_0(r,\theta)\}^2$$

This expression is transformed as follows:

$$\Delta H = \sum_{r,\theta} \{\Delta p(r,\theta)^2 + 2\Delta p(r,\theta)[p(r,\theta) - p_0(r,\theta)]\} \quad \text{[Expression 106]}$$

Since Δf(x, y) has a value only at ($x_0$, $y_0$), Δp(r, θ) has a value of Δμ only at r(θ)=$x_0$ cos θ+$y_0$ sin θ and zero elsewhere. Therefore, the expression within the braces { } in Expression 106 has values only at r(θ)=$x_0$ cos θ+$y_0$ sin θ. Therefore, the sum of a series does not need to be calculated with respect to both r and θ, and Expression 106 can be expressed as follows:

$$\Delta H = \sum_{\theta} \{\Delta\mu^2 + 2\Delta\mu[p(r(\theta),\theta) - p_0(r(\theta),\theta)]\} \quad \text{[Expression 107]}$$

Importantly, Expression 107 is the sum of a series only with respect to θ. As a result, the amount of calculation can be significantly reduced. Since p and $p_0$ are digital images, interpolation with respect to r(θ) is necessary in advance to the summation in Expression 107. Therefore, the expression within the braces { } in Expression 107 cannot be further expanded. Despite this, if Expression 107 is expanded while admitting errors, the following expression is obtained:

$$\Delta H = M\Delta\mu^2 + 2\Delta\mu \sum_{\theta} \{p(r(\theta),\theta) - p_0(r(\theta),\theta)\} \quad \text{[Expression 108]}$$

Note that M represents the number of projection angles. If Expression 108 is used instead of Expression 107, the value of ΔH has an error of about 1%. However, Expression 108 can be calculated more quickly than Expression 107, and therefore, is highly useful in the present invention.

Next, calculation of Δσ will be described. The standard deviation of luminance values in an area around the coordinate point ($x_0$, $y_0$) is represented by σ. The area around ($x_0$, $y_0$) is assumed to be d×d pixels around ($x_0$, $y_0$) (in this example, d=5). The standard deviation of these pixels can be obtained as follows:

$$\sigma = \sqrt{\langle f(x_0,y_0)^2\rangle - \langle f(x_0,y_0)\rangle^2}$$ [Expression 109]

where:

$$\langle f(x_0, y_0)^2 \rangle = \frac{1}{d^2} \sum_{i,j=-d/2}^{d/2} f(x_0 + i, y_0 + j)^2$$ [Expression 110]

$$\langle f(x_0, y_0) \rangle = \frac{1}{d^2} \sum_{i,j=-d/2}^{d/2} f(x_0 + i, y_0 + j)$$ [Expression 111]

By using Expressions 109 to 111, $\Delta\sigma$ can be calculated as follows:

$$\Delta\sigma = \sqrt{\langle f(x_0,y_0)^2\rangle - \frac{f_i^2 - f_j^2}{d^2} - \left\{\langle f(x_0,y_0)\rangle - \frac{f_i - f_j}{d^2}\right\}^2}$$ [Expression 112]

Note that $f_i$ and $f_j$ represent values of $f(x_0, y_0)$ before and after changing.

The definition of the entropy S will be described before the following calculation of $\Delta S$ will be described. In general, images handled by computers are digital images. Not only the coordinates (x, y) of pixels, but also the values of the pixels have digital values. Therefore, it can be assumed that a pixel is a quantum and that a pixel value is a quantum state. In this sense, an image can be considered as a kind of quantum ensemble. According to statistical mechanics, the entropy of such a system is defined as follows:

$$S = k\ln\frac{N!}{N_1!N_2!\ldots N_i!\ldots N_n!}$$ [Expression 113]

In Expression 113, N represents the total number of pixels in an image, $N_i$ represents the total number of pixels having a pixel value of i, which is a digital value, and k represents the Boltzmann constant in typical physics, but here, any value since the present invention is not directly related to physics. In the present invention, S is also assumed to be defined in the area of d×d pixels around $(x_0, y_0)$ as is similar to $\sigma$.

A differential $\Delta S$ of S defined in Expression 113 is considered. It is assumed that by changing, a pixel value (digital value) is changed from i to j. In this case, $\Delta S$ can be written as follows:

$$\Delta S = k\ln\frac{N!}{N_1!N_2!\ldots(N_i-1)!\ldots(N_j+1)!\ldots N_n!} - k\ln\frac{N!}{N_1!N_2!\ldots N_i!\ldots N_j!\ldots N_n!}$$ [Expression 114]

Thus, by changing, $N_i$ is decreased by one while $N_j$ is increased by one. If Expression 114 is expanded, a considerably simple expression is obtained as follows:

$$\Delta S = k\ln N_i - k\ln(N_j+1)$$ [Expression 115]

In summary, the procedure of this embodiment is as follows.

(I) Using random numbers, $(x_0, y_0)$ and $\Delta\mu$ are selected.
(II) Using Expressions 104, 108 (or 107), 112 and 115, $\Delta E$ is calculated.
(III) If the result of evaluation is improved ($\Delta E<0$), $\Delta\mu$ is added to $f(x_0, y_0)$.
(IV) If $\Delta E>0$, $\Delta\mu$ is also added to $f(x_0, y_0)$ with a probability of $\exp(-\Delta E/T)$.
(V) The temperature T is decreased by a small amount.
(VI) The procedure above is repeated from (I).
(VII) If the predetermined stop conditions are satisfied, the process is ended. For example, the stop condition may be that the probability of success becomes lower than a predetermined value (e.g., 10%, this value is adjustable appropriately) where "success" means the case when $\Delta\mu$ is added in (III) and (IV). An estimated cross-sectional image at the end of the process is considered as a cross-sectional image of the target object, which may be displayed on a display of the computer or may be recorded into a recording medium.

It is seen that steps (I) to (VI) faithfully correspond to basic steps (i) to (vi) of SA. Note that the processes in steps (I) to (VII) are performed in the image reconstruction processor of FIG. 1.

Note that the end of the process in step (VII) may not be performed in the image reconstruction processor of FIG. 1. Estimated cross-sectional images may be successively displayed on a display of the computer, and a user who views the images may stop the process.

Third Embodiment

Next, an important variation of the aforementioned method will be described. In the aforementioned method, Expression 107 or 108 is used to obtain the sum of a series with respect to θ. Therefore, each Monte Carlo step includes M times of summation. On the other hand, this embodiment is provided to further reduce the amount of calculation.

Firstly, a back projection g(x, y) of p(r, θ) will be considered.

$$g(x, y) = \sum_{\theta} p(x\cos\theta + y\sin\theta, \theta)$$ [Expression 116]

In Expression 116, since a filtering operation is not performed, g(x, y) becomes a similar image to the cross-sectional image f(x, y), but significantly blurred. If g(x, y) is used, Expression 108 is written as follows:

$$\Delta H = M\Delta\mu^2 + 2\Delta\mu\{g(x_0, y_0) - g_0(x_0, y_0)\}$$ [Expression 117]

Note that $g_0(x, y)$ is a back projection of $p_0(r, \theta)$ and is calculated in the manner similar to that of Expression 116. Expression 117 is superior to Expression 108 in terms of the absence of summation. Since $g_0(x, y)$ does not change at all during the calculation process, $g_0(x, y)$ can be calculated in advance. On the other hand, g(x, y) changes a little for every time a point of f(x, y) is changed, and therefore, to be exact, needs to be recalculated every time when a set of steps (I) to (IV) is executed. However, if it is assumed that the change in g(x, y) due to the change in f(x, y) is small, another set of steps is applicable, which is of this embodiment. The steps of this embodiment will be hereinafter described. Note that steps (1) to (9) below are performed in the image reconstruction processor of FIG. 1.

(1) $g_0(x, y)$ is obtained from $p_0(r, \theta)$.
(2) p(r, θ) is calculated from f(x, y), and then g(x, y) is obtained from p(r, θ).
(3) An image $\Delta\mu(x, y)$ whose pixel value is a change value of f(x, y) is generated using a random number.

(4) Expression 117 is applied to each pixel value to calculate an image $\Delta H(x, y)$.

(5) Similarly, Expressions 112 and 115 are applied to each pixel value to calculate images $\Delta\sigma(x, y)$ and $\Delta S(x, y)$.

(6) $\Delta E(x, y)$ is calculated based on Expression 104.

(7) $\Delta\mu(x, y)$ is set to 0 for a coordinate point $(x, y)$ having a positive $\Delta E$.

(8) $\Delta u(x, y)$ is added to $f(x, y)$.

(9) T is multiplied by $\alpha(\alpha<1)$, and the procedure is repeated from (2).

(10) If the predetermined stop conditions are satisfied, the process is ended. For example, the stop condition may be that the probability of success becomes lower than a predetermined value (e.g., 10%, this value is adjustable appropriately) where "failure" means the case when $\Delta\mu(x, y)$ is set to 0. An estimated cross-sectional image at the end of the process is considered as a cross-sectional image of the target object, which may be displayed on a display of the computer or may be recorded into a recording medium.

Note that the determination of whether to end the process in step (10) may not be performed in the image reconstruction processor of FIG. 1. Estimated cross-sectional images may be successively displayed on a display of the computer, and a user who views the images may instruct the computer to end the process.

Schematic concepts of steps (I) to (VII) and steps (1) to (10) are schematically shown in FIG. 5. In FIG. 5, an axis represents a value of a parameter (in this case, a value of a pixel), and the virtual energy E is represented by a gray level (a higher gray level indicates a smaller E). For the sake of convenience, the number of parameters (the number of pixels) is assumed to be two. In the case of steps (I) to (VII) shown in FIG. 5(a), a minimum value of E is eventually reached via a zigzag path while sometimes directs a wrong direction. On the other hand, in the case of steps (1) to (10) of FIG. 5(b), a minimum value of E is searched for while the gradient of E is taken into consideration. The method of FIG. 5(b) would be intuitively recognized as being more efficient. This embodiment is advantageous in terms of calculation speed because of a reduction in the amount of calculation by Expression 117 and an improvement in search efficiency shown in FIG. 5(b). Note that steps (1) to (10) do not faithfully correspond to the basic algorithm (i) to (vi) of SA, and are a natural expansion of steps (I) to (VII).

Other Embodiments

An image reconstruction processor for executing the process described in each embodiment above can be implemented using a program for causing a computer to execute these processes, a computer in which the program is installed, a specialized LSI for executing these processes, or the like.

EXAMPLES

As an example, the effect of removing a metal artifact using simulation will be described. Firstly, for comparison, results from the technique of Non-Patent Document 1 are shown in FIG. 6 (FIG. 5 in Non-Patent Document 1).

In FIG. 6, results (a), (d) and (g) in the left column are original phantom images without a metal artifact. Results (b), (e) and (h) in the middle column are images reconstructed by a typical FBP method, where invisible regions are set at predetermined positions in the original phantom images. Results (c), (f) and (i) in the right column are images reconstructed by the method of Non-Patent Document 1, where opaque regions are set as in results (b), (e) and (h). The results (c), (f) and (i) are one of the best achievements in removal of metal artifacts by the conventional arts.

Figure 7:
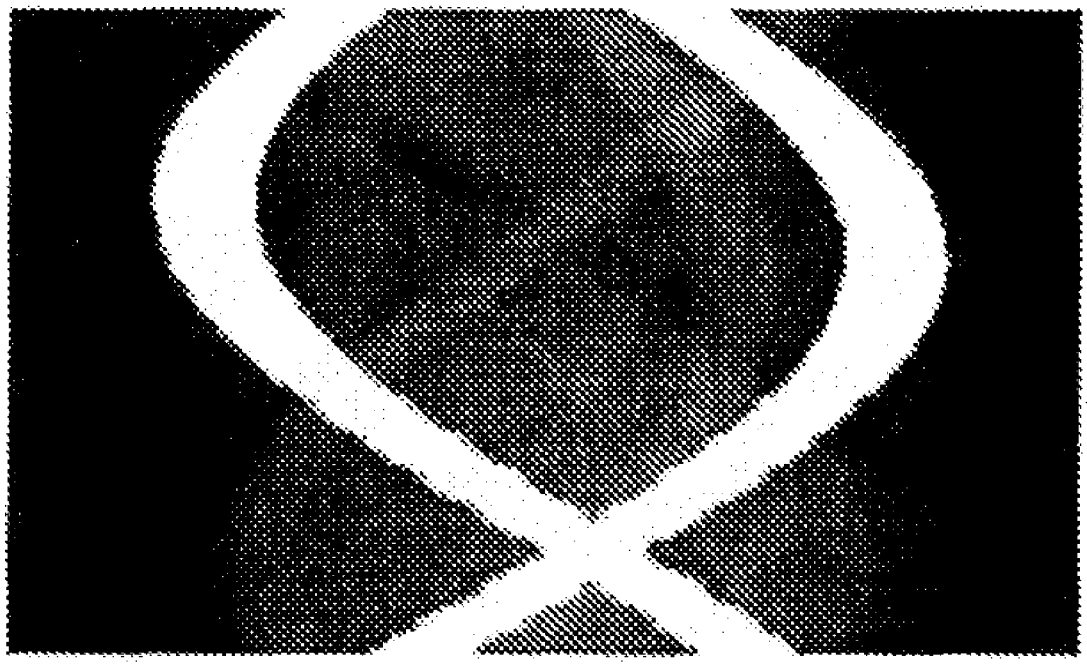
FIG. 7 is a sinogram obtained from FIG. 6(a) by simulation (a white portion is an opaque region).
Figure 8:
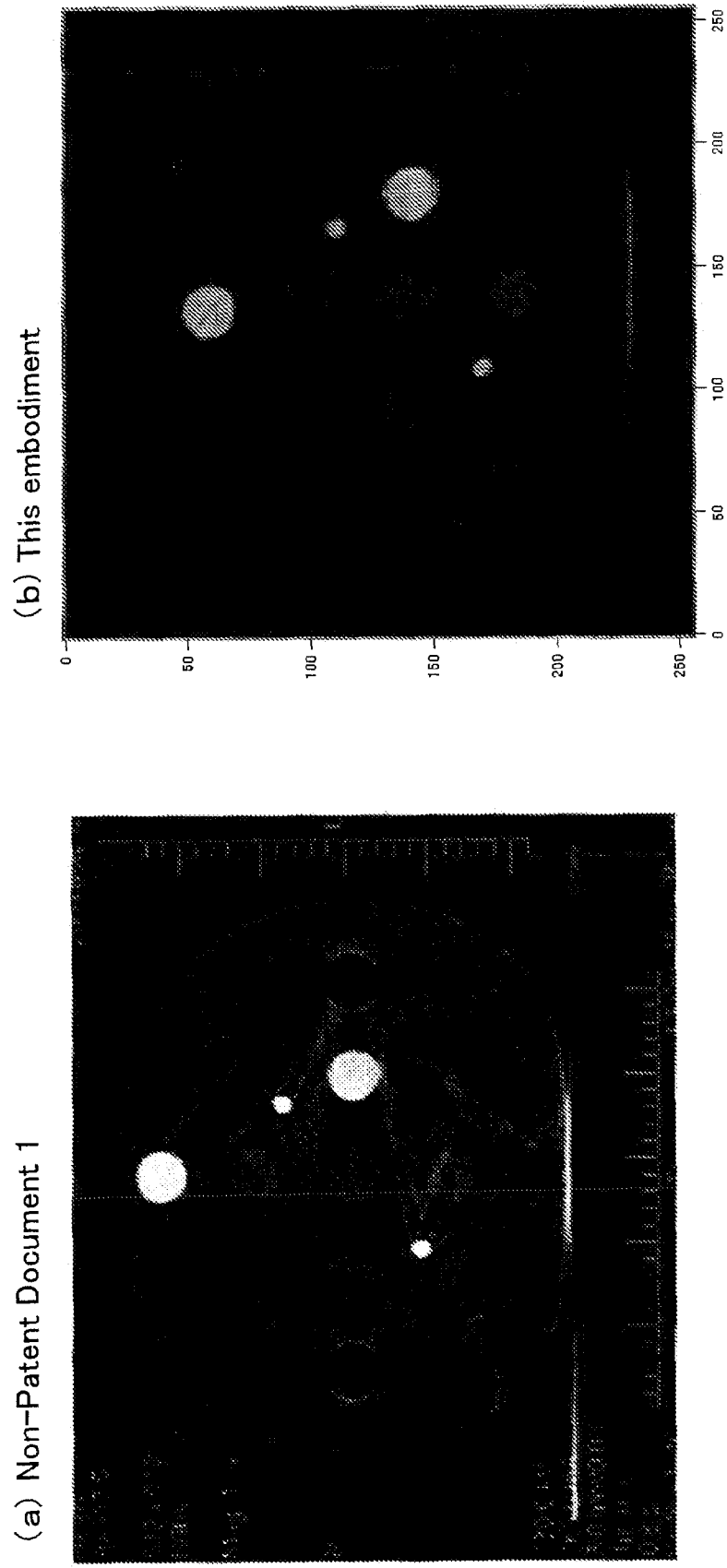
FIG. 8(a) is an enlarged diagram of FIG. 6(c).
FIG. 8(b) is a diagram showing a result of the present invention.

The image of FIG. 6(a) in Non-Patent Document 1 was used, and the opaque regions were set at the same positions as those in the document. Then, projections were calculated by simulation. The result is shown in FIG. 7. FIG. 7 corresponds to $p_0(r, \theta)$ of this example. An image reconstructed from FIG. 7 by the present invention and an enlarged diagram of FIG. 6(c) for comparison are shown in FIG. 8. The effect of the present invention can be clearly seen from FIG. 8. In FIG. 8(b) of this embodiment, it is difficult to find even a feature of metal artifacts.

Note that, in FIG. 8(b) of this embodiment, edge portions are slightly blurred. This is because a "factor which smoothes a cross-sectional image" (smoothing term $c\sigma$) is strong to some extent. It is known that the factor needs to be set to be strong to some extent so as to reduce metal artifacts. In any case, according to this embodiment, metal artifacts can be considerably removed, although there is still room for an improvement in the balance between each factor when the virtual energy E is calculated.

Figure 9:
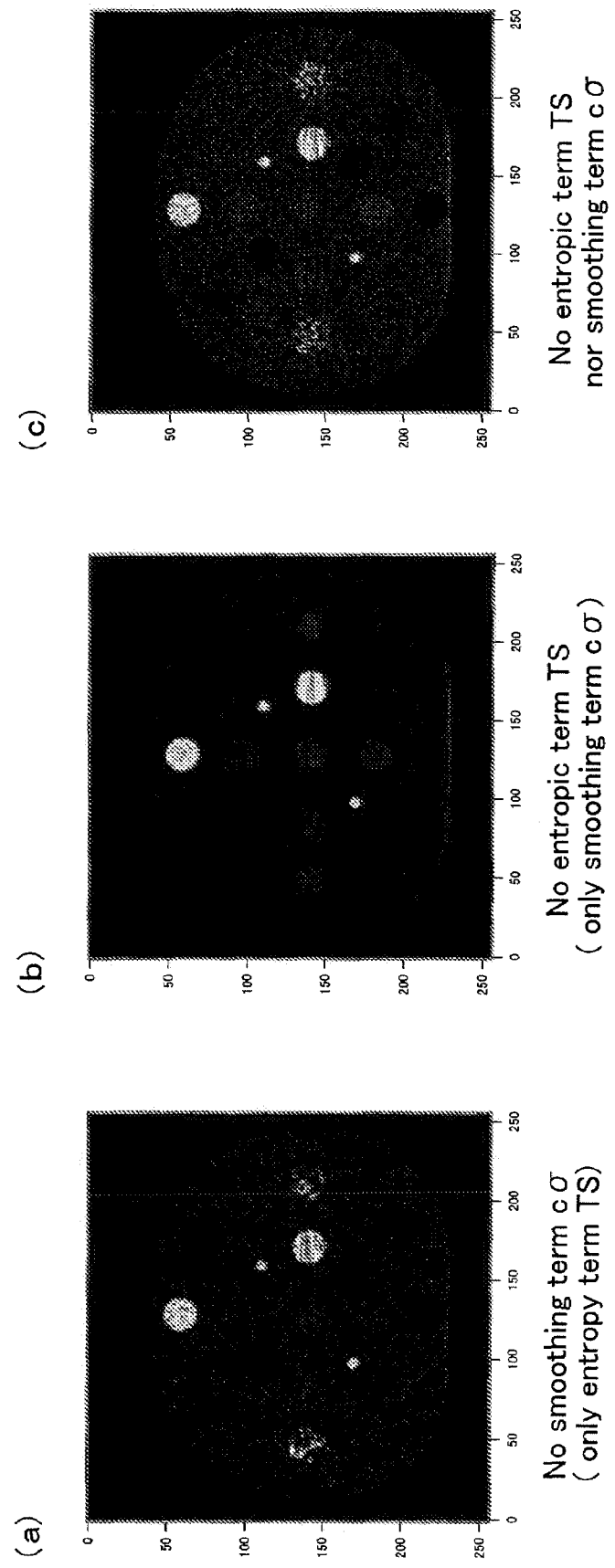
FIG. 9 is a schematic diagram showing an effect of each term in a virtual energy E.

Note that, for reference, a result obtained by executing the algorithm of this embodiment without setting the smoothing term $c\sigma$ or the entropic term TS is shown in FIG. 9. FIG. 9(a) shows a result obtained in the absence of the smoothing term $c\sigma$ (in the presence of only the entropic term TS), FIG. 9(b) shows a result obtained in the absence of the entropic term TS (in the presence of only the smoothing term $c\sigma$), and FIG. 9(c) shows a result obtained in the absence of both the entropic term TS and the smoothing term $c\sigma$. When FIG. 9 is compared to FIG. 8(b), it is found that, in this embodiment, metal artifacts can be removed to a greater extent when both smoothing term $c\sigma$ and the entropic term TS are introduced to the energy E than when only either of them is set and when none of them is set. When only the smoothing term is set, streaks extending radially from an opaque region are left as artifacts. On the other hand, when only the entropic term is set, a cross-sectional image becomes granular and has a low S/N. For final image quality, the ratio of the coefficient c of the smoothing term and the virtual temperature T during a slow cooling process seems to be important.

Next, an example with the limitation on a rotational angle is shown in FIG. 10. FIG. 10(a) shows a result from reconstruction only by FBP (typical CT). FIG. 10(b) shows a result from application of ILST (an image reconstruction method based on the least square method). FIG. 10(c) shows a result from reconstruction by this embodiment. When these results are compared, it is found that this embodiment is effective against artifacts which appear in the case of the limitation. Artifacts due to the angle limitation are characterized in that a circular region is altered to an almond-shaped region having two opposite sharp ends and luminance is reversed across round side edges connecting the sharp ends of the almond-shaped region. In this embodiment, both of the characteristics are reduced.

INDUSTRIAL APPLICABILITY

The present invention is significantly effective against metal artifacts, and therefore, is particularly useful in a field where metal artifacts are serious, such as CT for teeth, CT for an object including a metal implant, or the like.

Also, the present invention is generally effective in reconstruction from a set of projections having a lack of information. For example, there is a significant lack of information when there is a limit on a projection angle. The projection angle limitation causes a problem with three-dimensional electron microscopy, CT mammography, translation CT (Japanese Unexamined Patent Application Publication No. 2006-71472) or the like. The lack-of-information problem also occurs in three-dimensional CT, such as cone beam CT, helical scan CT or the like. The present invention is also effective in removal of artifacts appearing in three-dimensional CT.

Moreover, the present invention is applicable to a system in which the amount of information is considerably small. For example, the present invention is useful for fluorescent X-ray CT, seismic CT for imaging Earth's interior, and the like.

The present invention also has a subsidiary benefit that a luminance value (corresponding to an absorption coefficient in the case of X-ray) in a cross-sectional image can be determined with higher accuracy than that of the conventional art, for example. This effect can be applied so as to improve the accuracy of measurement of bone density or the like.

The present invention can be used to obtain a reconstructed image having a higher contrast than that of the conventional art. Therefore, the present invention is also highly useful for typical X-ray CT in which artifacts or the like do not cause a problem. Also, since the present invention is stable even when there is a shortage of data, the present invention is effective in a reduction in time required for measurement of projections, and therefore, a reduction in X-ray dose. According to these features, the present invention has the potential to replace all existing X-ray CT techniques.

The invention claimed is:

1. An image reconstructing device for obtaining a cross-sectional image of an object from projections (hereinafter referred to as "radiographic projections") obtained by irradiating the object with a beam of radiation, comprising:
   means (a) for obtaining an evaluation function (hereinafter referred to as an "energy") ($E_0$) including differences between projections calculated from a current estimated cross-sectional image of the object and the radiographic projections;
   means (b) for modifying a portion of the current estimated cross-sectional image;
   means (c) for obtaining an energy ($E_1$) including differences between projections calculated from the modified estimated cross-sectional image and the radiographic projections;
   means (d) for obtaining a differential ($\Delta E$) between the energy ($E_0$) and the energy ($E_1$);
   means (e) for determining whether or not the modification is to be accepted, based on an acceptance function using the differential ($\Delta E$) and a temperature parameter (T) for controlling an acceptance probability, and reflecting a result of the determination on the current estimated cross-sectional image; and
   means (f) for changing a value of the temperature parameter (T) every time the number of iterations of a series of processes of the means (a) to (e) reaches a predetermined value.

2. The image reconstructing device of claim 1, wherein
   the means (a) calculates an energy ($E_0$) including a sum of differences between projections calculated from the current estimated cross-sectional image and the radiographic projections, and a standard deviation of a local region of the current estimated cross-sectional image, and
   the means (c) calculates an energy ($E_1$) including a sum of differences between projections calculated from the modified estimated cross-sectional image and the radiographic projections, and a standard deviation of a local region of the modified estimated cross-sectional image.

3. The image reconstructing device of claim 1, wherein
   the means (a) calculates an energy ($E_0$) including a sum of differences between projections calculated from the current estimated cross-sectional image and the radiographic projections, and an entropy of a local region of the current estimated cross-sectional image, and
   the means (c) calculates an energy ($E_1$) including a sum of differences between projections calculated from the modified estimated cross-sectional image and the radiographic projections, and an entropy of a local region of the modified estimated cross-sectional image.

4. The image reconstructing device of claim 1, wherein
   the means (a) calculates an energy ($E_0$) including a sum of differences between projections calculated from the current estimated cross-sectional image and the radiographic projections, a standard deviation of a local region of the current estimated cross-sectional image, and an entropy of the local region of the current estimated cross-sectional image, and
   the means (c) calculates an energy ($E_1$) including a sum of differences between projections calculated from the modified estimated cross-sectional image and the radiographic projections, a standard deviation of a local region of the modified estimated cross-sectional image, and an entropy of the local region of the modified estimated cross-sectional image.

5. The image reconstructing device of claim 1, comprising:
   instead of the means (a), (c) and (d),
   means (h) for calculating $\Delta H$ using [Expression 1], and obtaining $\Delta E$ ($\Delta E = \Delta H + \ldots$) including the calculated $\Delta H$ as a component, $$\Delta H = \sum_\theta \{\Delta\mu^2 + 2\Delta\mu[p(r(\theta), \theta) - p_0(r(\theta), \theta)]\} \quad \text{[Expression 1]}$$

where, when the current estimated cross-sectional image of the object is represented by f(x, y) and the portion modified by the means (b) is represented by $\Delta f(x, y)$, $\Delta f(x, y)$ is a cross-sectional image having a value of $\Delta\mu$ only at a coordinate point ($x_0$, $y_0$) and zero elsewhere, and p(r, $\theta$) represents a projection calculated from the current estimated cross-sectional image of the object, $p_0$(r, $\theta$) represents a radiographic projection of the object, r represents a channel position of a one-dimensional detector taking the projection, $\theta$ represents a projection angle, and $r(\theta) = x_0 \cos\theta + y_0 \sin\theta$.

6. The image reconstructing device of claim 5, wherein
   the means (h) calculates $\Delta\sigma$ using [Expression 3], and obtains $\Delta E$ ($\Delta E = \Delta H + c\Delta\sigma + \ldots$) including as a component a sum of a product ($c\Delta\sigma$) of the calculated $\Delta\sigma$ and a coefficient c, and the $\Delta H$, $$\Delta\sigma = \sqrt{\langle f(x_0, y_0)^2\rangle - \frac{f_i^2 - f_j^2}{d^2} - \left\{\langle f(x_0, y_0)\rangle - \frac{f_i - f_j}{d^2}\right\}^2} \quad \text{[Expression 3]}$$

where $\sigma$ represents a standard deviation of luminance values of d×d pixels around the coordinate point ($x_0$, $y_0$) and is calculated by [Expression 4], and $f_i$ and $f_j$ represent values of $f(x_0, y_0)$ before and after the modification by the means (b), $$\sigma = \sqrt{\langle f(x_0, y_0)^2 \rangle - \langle f(x_0, y_0) \rangle^2} \quad \text{[Expression 4]}$$
where $$\langle f(x_0, y_0)^2 \rangle = \frac{1}{d^2} \sum_{i,j=-d/2}^{d/2} f(x_0 + i, y_0 + j)^2 \quad \text{[Expression 5]}$$

$$\langle f(x_0, y_0) \rangle = \frac{1}{d^2} \sum_{i,j=-d/2}^{d/2} f(x_0 + i, y_0 + j). \quad \text{[Expression 6]}$$

7. The image reconstructing device of claim 5, wherein the means (h) calculates $\Delta S$ using [Expression 7], and obtains $\Delta E$ ($\Delta E = \Delta H - T\Delta S + \ldots$) including as a component a sum of a product ($-T\Delta S$) of the calculated $\Delta S$ and the temperature parameter (T), and the $\Delta H$, $$\Delta S = k \ln N_i - k \ln(N_j + 1) \quad \text{[Expression 7]}$$

where S represents an entropy of a local region image of d×d pixels around the coordinate point $(x_0, y_0)$ and is calculated by [Expression 8], $$S = k \ln \frac{N!}{N_1! N_2! \ldots N_i! \ldots N_n!} \quad \text{[Expression 8]}$$

where
N: a total number of pixels in the local region image,
$N_i$: a total number of pixels whose pixel value is a digital value of i,
$N_j$: a total number of pixels whose pixel value is a digital value of j,
k: a constant,
a pixel value is changed from the digital value i to the digital value j by the modification by the means (b).

8. The image reconstructing device of claim 1, comprising:
instead of the means (a), (c) and (d),
means (h) for calculating $\Delta H$ using [Expression 1], and obtaining $\Delta E$ ($\Delta E = \Delta H + \ldots$) including the calculated $\Delta H$ as a component, $$\Delta H = M\Delta\mu^2 + 2\Delta\mu \sum_{\theta} \{p(r(\theta), \theta) - p_0(r(\theta), \theta)\} \quad \text{[Expression 2]}$$

where, when the current estimated cross-sectional image of the object is represented by $f(x, y)$ and the portion modified by the means (b) is represented by $\Delta f(x, y)$, $\Delta f(x, y)$ is a cross-sectional image having a value of $\Delta\mu$ only at a coordinate point $(x_0, y_0)$ and zero elsewhere, and $p(r, \theta)$ represents a projection calculated from the current estimated cross-sectional image of the object, $p_0(r, \theta)$ represents a radiographic projection of the object, r represents a channel position of a one-dimensional detector taking the projection, $\theta$ represents a projection angle, $r(\theta) = x_0 \cos\theta + y_0 \sin\theta$, and M represents the number of projection angles.

9. The image reconstructing device of claim 8, wherein the means (h) calculates $\Delta\sigma$ using [Expression 3], and obtains $\Delta E$ ($\Delta E = \Delta H + c\Delta\sigma + \ldots$) including as a component a sum of a product ($c\Delta\sigma$) of the calculated $\Delta\sigma$ and a coefficient c, and the $\Delta H$, $$\Delta\sigma = \sqrt{\langle f(x_0, y_0)^2 \rangle - \frac{f_i^2 - f_j^2}{d^2} - \left\{ \langle f(x_0, y_0) \rangle - \frac{f_i - f_j}{d^2} \right\}^2} \quad \text{[Expression 3]}$$

where $\sigma$ represents a standard deviation of luminance values of d×d pixels around the coordinate point $(x_0, y_0)$ and is calculated by [Expression 4], and $f_i$ and $f_j$ represent values of $f(x_0, y_0)$ before and after the modification by the means (b), $$\sigma = \sqrt{\langle f(x_0, y_0)^2 \rangle - \langle f(x_0, y_0) \rangle^2} \quad \text{[Expression 4]}$$
where $$\langle f(x_0, y_0)^2 \rangle = \frac{1}{d^2} \sum_{i,j=-d/2}^{d/2} f(x_0 + i, y_0 + j)^2 \quad \text{[Expression 5]}$$

$$\langle f(x_0, y_0) \rangle = \frac{1}{d^2} \sum_{i,j=-d/2}^{d/2} f(x_0 + i, y_0 + j). \quad \text{[Expression 6]}$$

10. The image reconstructing device of claim 8, wherein the means (h) calculates $\Delta S$ using [Expression 7], and obtains $\Delta E$ ($\Delta E = \Delta H - T\Delta S + \ldots$) including as a component a sum of a product ($-T\Delta S$) of the calculated $\Delta S$ and the temperature parameter (T), and the $\Delta H$, $$\Delta S = k \ln N_i - k \ln(N_j + 1) \quad \text{[Expression 7]}$$

where S represents an entropy of a local region image of d×d pixels around the coordinate point $(x_0, y_0)$ and is calculated by [Expression 8], $$S = k \ln \frac{N!}{N_1! N_2! \ldots N_i! \ldots N_n!} \quad \text{[Expression 8]}$$

where
N: a total number of pixels in the local region image,
$N_i$: a total number of pixels whose pixel value is a digital value of i,
$N_j$: a total number of pixels whose pixel value is a digital value of j,
k: a constant,
a pixel value is changed from the digital value i to the digital value j by the modification by the means (b).

11. The image reconstructing device of claim 1, comprising:
instead of the means (e) and (f), means (e1) for determining whether or not the modification is to be accepted, based on an acceptance function using the differential ($\Delta E$) and a temperature parameter (T) for controlling an acceptance probability, and reserving reflection of a result of determination on the current estimated cross-sectional image; and
means (f1) for reflecting the reservation(s) in the means (e1) on the current estimated cross-sectional image and changing a value of the temperature parameter (T) every time the number of iterations of a series of processes of the means (a) to (d) and (e1) reaches a predetermined value.

12. An image reconstructing device for obtaining a cross-sectional image of an object from projections obtained by irradiating the object with a beam of radiation, comprising:
- means (m1) for calculating a back projection $g_0(x, y)$ of a radiographic projection $p_0(r, \theta)$ of the object by a back projection operation without filtering;
- means (m2) for calculating a projection $p(r, \theta)$ from a current estimated cross-sectional image $f(x, y)$ of the object, and calculating a back projection $g(x, y)$ of the projection $p(r, \theta)$ by a back projection operation without filtering;
- means (m3) for generating an image $\Delta\mu(x, y)$ whose pixel value is a change value of the current estimated cross-sectional image $f(x, y)$ of the object;
- means (m4) for generating an image $\Delta H(x, y)$ by applying [Expression 9] to each pixel value, $$\Delta H = M\Delta\mu^2 + 2\Delta\mu\{g(x_0, y_0) - g_0(x_0, y_0)\} \quad \text{[Expression 9]}$$

where
M: the number of projection angles;
- means (m5) for calculating $\Delta E(x, y)$ using the $\Delta H(x, y)$, where
  $\Delta E(x, y)$ represents a differential between evaluation functions $E_0(x, y)$ and $E_1(x, y)$,
  $E_0(x, y)$ represents an evaluation function including a difference between the projection $p(r, \theta)$ calculated from the estimated cross-sectional image $f(x, y)$ and the radiographic projection $p_0(r, \theta)$, and
  $E_1(x, y)$ represents an evaluation function including a difference between a projection $\{p(r, \theta) + \Delta p(r, \theta)\}$, calculated from a sum $\{f(x, y) + \Delta\mu(x, y)\}$ of the estimated cross-sectional image $f(x, y)$ and the image $\Delta\mu(x, y)$ obtained by the means (m3), and the radiographic projection $p_0(r, \theta)$;
- means (m6) for setting the $\Delta\mu(x, y)$ to 0 at a coordinate point $(x, y)$ where the $\Delta E$ is positive; and
- means (m7) for setting a sum of the estimated cross-sectional image $f(x, y)$ and the image $\Delta\mu(x, y)$ obtained by the means (m6) as a new estimated cross-sectional image $f(x, y)$ and repeating processes of the means (m2) to (m6) with respect to the new estimated cross-sectional image $f(x, y)$.

13. An image reconstructing device for obtaining a cross-sectional image of an object from projections obtained by irradiating the object with a beam of radiation, comprising:
- means (m1) for calculating a back projection $g_0(x, y)$ of a radiographic projection $p_0(r, \theta)$ of the object using [Expression 10]

$$g_0(x, y) = \sum_\theta p_0(x\cos\theta + y\sin\theta, \theta) \quad \text{[Expression 10]}$$

r: a channel position of a one-dimensional detector taking the projection,
$\theta$: a projection angle,
- means (m2) for calculating a projection $p(r, \theta)$ from a current estimated cross-sectional image $f(x, y)$ of the object, and calculating a back projection $g(x, y)$ of the projection $p(r, \theta)$ using [Expression 11]

$$g(x, y) = \sum_\theta p(x\cos\theta + y\sin\theta, \theta) \quad \text{[Expression 11]}$$

- means (m3) for generating an image $\Delta\mu(x, y)$ whose pixel value is a change value of the current estimated cross-sectional image $f(x, y)$ of the object;
- means (m4) for generating an image $\Delta H(x, y)$ by applying [Expression 12] to each pixel value, $$\Delta H = M\Delta\mu^2 + 2\Delta\mu\{g(x_0, y_0) - g(x_0, y_0)\} \quad \text{[Expression 12]}$$

where
M: the number of projection angles;
- means (m5) for generating $\Delta\sigma(x, y)$ by applying [Expression 13] to each pixel value, $$\Delta\sigma = \sqrt{\langle f(x_0, y_0)^2\rangle - \frac{f_i^2 - f_j^2}{d^2} - \left\{\langle f(x_0, y_0)\rangle - \frac{f_i - f_j}{d^2}\right\}^2} \quad \text{[Expression 13]}$$

where $\sigma$ represents a standard deviation of luminance values of $d \times d$ pixels around a coordinate point $(x_0, y_0)$ and is calculated by [Expression 14], and $f_i$ and $f_j$ represent values of $f(x_0, y_0)$ before and after a change, $$\sigma = \sqrt{\langle f(x_0, y_0)^2\rangle - \langle f(x_0, y_0)\rangle^2} \quad \text{[Expression 14]}$$

where $$\langle f(x_0, y_0)^2\rangle = \frac{1}{d^2}\sum_{i,j=-d/2}^{d/2} f(x_0 + i, y_0 + j)^2 \quad \text{[Expression 15]}$$

$$\langle f(x_0, y_0)\rangle = \frac{1}{d^2}\sum_{i,j=-d/2}^{d/2} f(x_0 + i, y_0 + j) \quad \text{[Expression 16]}$$

- means (m6) for generating an image $\Delta S$ by applying [Expression 17] to each value, $$\Delta S = k \ln N_i - k \ln(N_j + 1) \quad \text{[Expression 17]}$$

where S represents an entropy of a local region image of $d \times d$ pixels around the coordinate point $(x_0, y_0)$ and is calculated by [Expression 18], $$S = k\ln\frac{N!}{N_1! N_2! \ldots N_i! \ldots N_n!} \quad \text{[Expression 18]}$$

where
N: a total number of pixels in the local region image,
$N_i$: a total number of pixels whose pixel value is a digital value of i,
$N_j$: a total number of pixels whose pixel value is a digital value of j,
k: a constant,
a pixel value is changed from the digital value i to the digital value j by the modification by the means (b);
- means (m7) for calculating $\Delta E(x, y)$ based on [Expression 19], $$\Delta E = \Delta H + c\Delta\sigma - T\Delta S \quad \text{[Expression 19]}$$

where
c: a coefficient,
T: a virtual temperature (temperature parameter),
- means (m8) for setting the $\Delta\mu(x, y)$ to 0 at a coordinate point $(x, y)$ where the $\Delta E$ is positive;

means (m9) for setting a sum of the estimated cross-sectional image f(x, y) and the image $\Delta\mu(x, y)$ obtained by the means (m8) as a new estimated cross-sectional image f(x, y); and means (m10) for multiplying the T by $\alpha(\alpha<1)$, and repeating processes of the means (m2) to (m9).

14. A method for obtaining a cross-sectional image of an object from projections (hereinafter referred to as "radiographic projections") obtained by irradiating the object with a beam of radiation, comprising the steps of:
   (a) obtaining an evaluation function (hereinafter referred to as an "energy") ($E_0$) including differences between projections calculated from a current estimated cross-sectional image of the object and the radiographic projections;
   (b) modifying a portion of the current estimated cross-sectional image;
   (c) obtaining an energy ($E_1$) including differences between projections calculated from the modified estimated cross-sectional image and the radiographic projections;
   (d) obtaining a differential ($\Delta E$) between the energy ($E_0$) and the energy ($E_1$);
   (e) determining whether or not the modification is to be accepted, based on an acceptance function using the differential ($\Delta E$) and a temperature parameter (T) for controlling an acceptance probability;
   (f) reflecting a result of the determination on the current estimated cross-sectional image, and returning to the step (a);
   (g) changing a value of the temperature parameter (T) every time the number of iterations of the steps (a) to (f) reaches a predetermined value; and
   (h) determining whether or not the result of the determination in the step (e) satisfies predetermined stop conditions, and if the result of the determination in the step (e) satisfies predetermined stop conditions, ending the process.

15. An image reconstructing program for obtaining a cross-sectional image of an object from projections (hereinafter referred to as "radiographic projections") obtained by irradiating the object with a beam of radiation, wherein
   the program causes a computer to execute the steps of:
   (a) obtaining an evaluation function (hereinafter referred to as an "energy") ($E_0$) including differences between projections calculated from a current estimated cross-sectional image of the object and the radiographic projections;
   (b) modifying a portion of the current estimated cross-sectional image;
   (c) obtaining an energy ($E_1$) including differences between projections calculated from the modified estimated cross-sectional image and the radiographic projections;
   (d) obtaining a differential ($\Delta E$) between the energy ($E_0$) and the energy ($E_1$);
   (e) determining whether or not the modification is to be accepted, based on an acceptance function using the differential ($\Delta E$) and a temperature parameter (T) for controlling an acceptance probability;
   (f) reflecting a result of the determination on the current estimated cross-sectional image, and returning to the step (a); and
   (g) changing a value of the temperature parameter (T) every time the number of iterations of the steps (a) to (f) reaches a predetermined value.

16. A CT apparatus comprising:
means (A) for obtaining projections by irradiating an object with a beam of radiation; and
means (B) for obtaining a cross-sectional image of the object from the projections,
wherein the means (B) includes:
   means (b1) for obtaining an evaluation function (hereinafter referred to as an "energy") ($E_0$) including differences between projections calculated from a current estimated cross-sectional image of the object and the projections by irradiating the object with the beam of radiation (hereinafter referred to as "radiographic projections");
   means (b2) for modifying a portion of the current estimated cross-sectional image;
   means (b3) for obtaining an energy ($E_1$) including differences between projections calculated from the modified estimated cross-sectional image and the radiographic projections;
   means (b4) for obtaining a differential ($\Delta E$) between the energy ($E_0$) and the energy ($E_1$);
   means (b5) for determining whether or not the modification is to be accepted, based on an acceptance function using the differential ($\Delta E$) and a temperature parameter (T) for controlling an acceptance probability, and reflecting a result of the determination on the current estimated cross-sectional image; and
   means (b6) for changing a value of the temperature parameter (T) every time the number of iterations of a series of processes of the means (b1) to (b5) reaches a predetermined value.

* * * * *